(12) United States Patent
Almberg

(10) Patent No.: US 8,123,734 B2
(45) Date of Patent: Feb. 28, 2012

(54) ABSORBENT ARTICLE

(75) Inventor: Christian Almberg, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 2040 days.

(21) Appl. No.: 10/225,203

(22) Filed: Aug. 22, 2002

(65) Prior Publication Data

US 2003/0060795 A1 Mar. 27, 2003

Related U.S. Application Data

(60) Provisional application No. 60/313,805, filed on Aug. 22, 2001.

(30) Foreign Application Priority Data

Aug. 22, 2001 (SE) ...................................... 0102805

(51) Int. Cl.
*A61F 13/15* (2006.01)

(52) U.S. Cl. ........ 604/392; 604/396; 604/386; 604/387; 604/385.24; 604/385.29; 604/385.3

(58) Field of Classification Search .................. 604/392, 604/396, 386, 387, 385.24, 385.29, 385.3
See application file for complete search history.

(56) References Cited

U.S. PATENT DOCUMENTS

| | | | |
|---|---|---|---|
| 4,041,203 A * | 8/1977 | Brock et al. | 428/157 |
| 5,188,885 A * | 2/1993 | Timmons et al. | 428/198 |

FOREIGN PATENT DOCUMENTS

| | | |
|---|---|---|
| EP | 0 287 388 A2 | 10/1988 |
| EP | 0 291 984 A1 | 11/1988 |
| EP | 0 409 307 B1 | 1/1991 |
| EP | 0474123 A1 | 3/1992 |
| EP | 0 605 012 B1 | 7/1994 |
| FR | 2 586 558 A1 | 6/1997 |
| JP | 05-169575 | 7/1993 |
| JP | 09-195154 | 7/1997 |
| JP | 10-057415 | 3/1998 |
| JP | 11-019128 | 1/1999 |
| JP | 11-075912 | 3/1999 |
| JP | 2000-054251 A | 2/2000 |
| JP | 2002-315607 A | 10/2002 |
| WO | 00/20206 | 4/2000 |
| WO | 00/27330 | 5/2000 |
| WO | 00/00129 A1 | 1/2001 |

* cited by examiner

*Primary Examiner* — Jacqueline F. Stephens
(74) *Attorney, Agent, or Firm* — Buchanan Ingersoll & Rooney PC

(57) ABSTRACT

An absorbent article such as a diaper and an incontinence guard provided with a pair of belt members (10*a*, 10*b*) attached to the rear portion (6), alternatively to the front portion, of the article and which are intended to be fastened together around the waist of the wearer by fastening means (11,12) and where the front portion (5), alternatively the rear portion, is provided with fasteners (8,9) intended to be fastened to the belt members (10*a*, 10*b*), in such a way that the article will assume a pantlike shape, where the belt members (10*a*, 10*b*) form a part of the waist portions of the pant. The belt members (10*a*, 10*b*) include a flexible laminate of at least two layers of fibrous material bonded together in a bonding pattern (13) provided by ultrasonic, laser and/or heat, the bonding pattern having a bonding area of no more than 10%, and the laminate having a tear strength of at least 22 N.

13 Claims, 1 Drawing Sheet

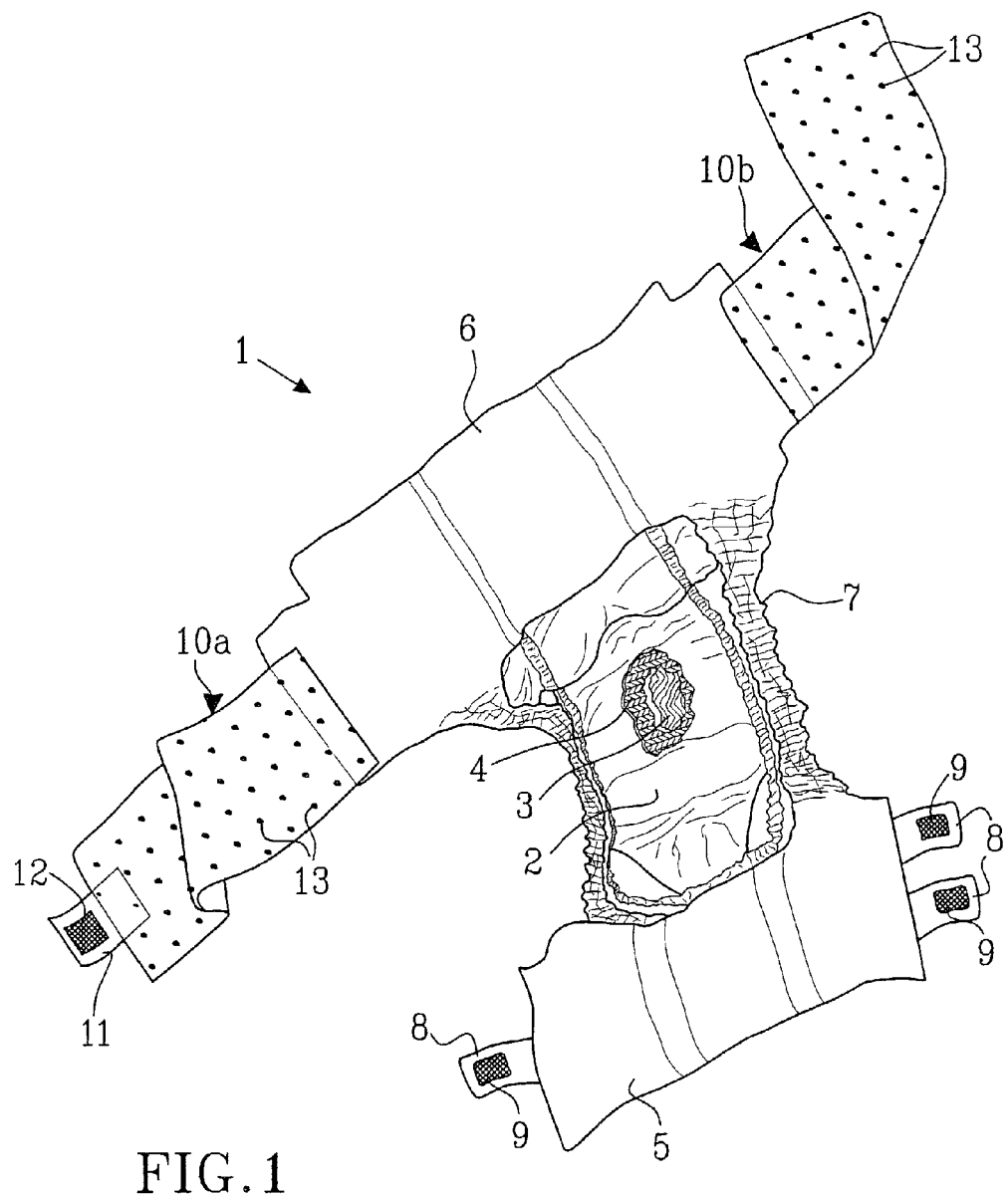
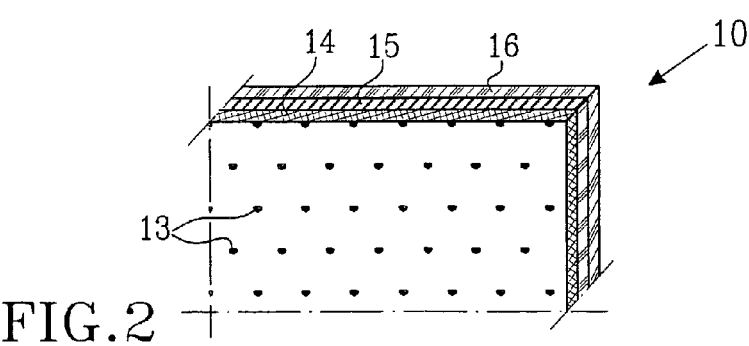
FIG.1
FIG.2

ABSORBENT ARTICLE

CROSS-REFERENCE TO RELATED APPLICATIONS

The present application claims the priority of U.S. Provisional Application No. 60/313,805, filed in the United States on Aug. 22, 2001, and to Swedish Application No. 0102805-9, filed in Sweden on Aug. 22, 2001, the entire contents of which are hereby incorporated herein by reference.

BACKGROUND OF THE INVENTION

1. Field of the Invention

The present invention relates to an absorbent article, such as a diaper or an incontinence guard comprising a liquid permeable topsheet, a liquid impermeable backsheet and an absorbent body enclosed therebetween, said article having a front portion, a rear portion and a crotch portion therebetween, and further is provided with a pair of belt members in such a way that the article will assume a pantlike shape.

2. Background Art

Diapers and incontinence guards for incontinent adults usually have a garment portion holding an absorbent body in place against the user's body and attachment means which hold the garment portion in place when the user is moving. A common type of attachment means are adhesive tapes or hook and loop fasteners of the touch-and-close type which directly attach front and rear portions of the absorbent article to each other. It is further known, through, e.g., EP-A-0 287 388, EP-A-0 409 307, EP-A-0 605 012 and FR-A-2 586 558, to attach the front and rear portions of the article by means of a belt. The belt members are usually attached to the rear portion of the diaper and are intended to be fastened together around the waist of the wearer, and fastening means provided at the front portion of the diaper are then intended to be fastened to the outside of the belt members. The belt provides improved possibilities to adjust the fit of the diaper. The belt further provides a simplified change of diaper or incontinence guard, especially when the wearer is standing.

One problem with these belts is that they may cause skin irritations to the user, because the belt is in direct contact with the skin of the wearer and has to be tightened relatively strongly in order to have a satisfactory fit and security against leakage of the diaper or incontinence guard. By the tight contact and friction between the belt and the skin there may be wear of the skin which gives rise to irritation and even skin injuries. It is therefor important that the material used to form the inside of the belt is soft and skin-friendly. Belt materials dealing with this problem are disclosed in WO 00/27330 and in WO 01/00129.

Another problem that may occur with belts is that they may tear when tightened around the wearer. This problem especially occurs for belts which are wholly made of fibrous material, often two or more layers of nonwoven materials bonded together into a laminate. Belts in which one layer is a plastic film are often strong, but they have a drawback of being tight and relatively stiff and therefor not so comfortable to wear.

OBJECTS AND SUMMARY

An object of the present invention is to provide a belt for absorbent articles which is comfortable to wear and which is resistant to tearing.

In one embodiment of the invention, the belt members comprise a flexible laminate of at least two layers of fibrous material bonded together in a bonding pattern provided by ultrasonic or laser welding and/or heat calendering, the bonding pattern having a bonding area of no more than 10%, and the laminate having a tear strength of at least 22 N.

According to one embodiment, the laminate has a tear strength of at least 24N, preferably at least 25 N and more preferably at least 30 N.

According to further preferred embodiments, the bonding pattern has a bonding area of no more than 8%, and preferably no more than 5%.

In a further embodiment of the invention, the bonding pattern has a density of bonding sites of between 1 and 15 bonding sites per $cm^2$, and preferably between 1 and 10 bonding sites per $cm^2$.

According to one embodiment, the laminate comprises at least three layers of fibrous material, one outer layer acting as a loop material for a hook-and-loop type fastener, a middle layer of a relatively tear strong fibrous material, and an inner layer of a soft and skin friendly fibrous material.

An example of a relatively tear strong fibrous material suited for the middle layer is a nonwoven material comprising continuous filaments, such as a spunbond and/or meltblown material.

According to one embodiment of the invention, the outer layer acts as an attachment surface for the fastening means, especially as a loop material for a hook-and-loop type fastener, is creped.

BRIEF DESCRIPTION OF DRAWINGS

FIG. 1 is a schematic perspective view of a belt-provided diaper according to an embodiment of the invention.

FIG. 2 is a schematically broken view of a laminate according to an embodiment of the invention.

PREFERRED EMBODIMENTS OF THE INVENTION

FIG. 1 of the drawings shows an embodiment of the present invention. A diaper or incontinence guard 1 comprises a liquid permeable topsheet 2, a liquid impermeable backsheet 3 and an absorbent body 4 enclosed therebetween. The liquid permeable topsheet 2 can be any material suitable for this purpose, for example a nonwoven material, such as a spunbond material of continuous filaments, a meltblown material, a thermobonded fibrous web such as a carded fibrous web. The topsheet may also be a layer of so tow fibers bonded in a bonding pattern or a perforated plastic film.

The liquid impermeable backsheet 3 may also be any material used for this purpose, such as a plastic film, a nonwoven material coated with a liquid impervious material, a hydrophobic nonwoven material which resists liquid penetration and/or a laminate of plastic film and nonwoven material. Breathable materials which are permeable to air and water vapour, but which resist liquid penetration at least up to a certain pressure may also be used as backsheet materials.

The topsheet 2 and the backsheet material 3 have a somewhat greater extension in the plane than the absorbent body 4 and extend outside the edges thereof. The layers 2 and 3 are connected to each other within the projecting portions thereof, e.g., by gluing or welding by heat or ultrasonic.

The absorbent body 4 can be of any kind suitable for this purpose. Examples of commonly used absorbent materials are cellulosic fluff pulp, tissue layers, highly absorbent polymers (so called superabsorbents), absorbent foam materials, absorbent nonwoven materials, or the like. It is common to combine cellulosic fluff pulp with superabsorbents in an absorbent body. It is also common to have absorbent bodies comprising layers of different materials with different properties with respect to liquid acquisition capacity, liquid distribution capacity and storage capacity. It is well-known to a person skilled in the art and does therefore not have to be described in detail. The thin absorbent bodies which are common in, for example, baby diapers and incontinence guards often comprise a compressed mixed or layered structure of cellulosic fluff pulp and superabsorbent.

The diaper is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The front portion 5 is provided with a pair of tabs 8 carrying attachment means such as a hook material 9 of a so called hook-and-loop type fastener, or other type of attachment means such as adhesive tape.

The term "hook material" is used to designate the portion of a mechanical fastening means having engaging "hook" elements. However it is not intended to limit the shape of the engaging elements to include only "hooks" but encompasses any shape of engaging elements, unidirectional or bidirectional, known in the art to mechanically engage a complementary loop fastening material.

A pair of belt members 10*a* and 10*b* have one end attached, e.g., glued or ultrasonically welded, to the rear part 6 of the diaper. The opposite ends of the belt members 10*a*, 10*b* are intended to be fastened together, e.g., by a tab 11, on one belt member 10*a*, the tab carrying a hook material 12 of a so called hook-and-loop type fastener. The hook material 12 on the tab 11 is intended to attach to the outside of the opposite belt member 10*b*. Instead of hook-and-loop type fastener 12 there may be another type of optional attachment means, such as adhesive tape.

The tabs 8 carrying a hook material or corresponding attachment means of the front portion 5 are intended to be attached to the outside of the belt members 10*a*, 10*b* in order to fasten together the diaper to the desired pantlike shape.

In an alternative embodiment the belt members 10*a*, 10*b* are attached to the front portion 5 of the diaper and are then fastened together at the back of the wearer. Tabs 8 carrying fastening means, for example a hook material or an adhesive tape, are in this case provided at the rear portion 6 of the diaper.

The outside of the belt members 10*a*, 10*b* should act as a reception surface cooperating with the fastening means on tabs 8 and 11. For hook-and-loop fasteners the material on the outside of the belt portions should serve as a loop material. The term "loop" in this respect is not limited only to materials in which discrete, separately formed loops of material are adapted to receive and engage the hook elements of a complementary hook material, but the loop material also includes fibrous nonwoven in which the individual fibers function to engage the hook elements without such fibers being formed into discrete loops.

For tape fasteners the material on the outside of the belt members 10*a*, 10*b* should serve as an attachment surface for adhesive tapes. Certain nonwoven materials will function both as loop material for hook-and-loop fasteners and as attachments surface admitting refastening of an adhesive tape. This is disclosed in WO 01/00129.

The width of the belt members should be between 5 and 20 cm, preferably between 7 and 15 cm.

The belt members according to this embodiment comprise a flexible laminate of at least two layers of fibrous material bonded together in a bonding pattern 13 provided by ultrasonic, laser and/or heat. At least some of the fibers in the layers of fibrous material should therefore be meltable by such bonding techniques. In one embodiment disclosed in FIG. 2, the laminate comprises three layers 14, 15 and 16. The bonding pattern 13 should preferably have a bonding area of no more than 10% and the laminate should preferably have a tear strength of at least 22 N. This will make the belt members resist tearing as the belt is tightened around the waist of the wearer. Tests have proven that the tearing frequency at normal use for belts having a tear strength of 21 N and lower was unacceptably high. Preferably, the tear strength should be at least 24 N, more preferably at least 25 N, and most preferably at least 27N. For those belts having a tear strength of 29 N or higher there was no tearing at all.

Tear strength

The tear strength is measured by EDANA test method TEAR 70.3-96, with the modification that a conditioning time of at least 4 h, a temperature of 23° C. and a relative humidity of 50% R.H. is used.

Bonding Area and Bonding Density

A bonding area of more than 10% may result in an increased amount of tearing indications or notches and an increased risk for tearing of the belt members.

Preferably the bonding area should be no more than 8%, and more preferably no more than 5%.

The bonding pattern comprises a plurality of bonding sites in the form of points, lines, spots, or the like, arranged in a pattern. The bonding area of a bonding pattern is defined as the amount of the pattern that consists of the bonding sites.

Another factor for providing high tear strength is the bonding density, which is the number of bonding sites per unit area. It is preferred that the bonding pattern 13 has a bonding density of between 1 and 15 bonding sites per $cm^2$. Preferably, it has a bonding density of between 1 and 10 bonding sites per $cm^2$. With a high bonding density, more tearing indications or notches are formed, which will deteriorate the tearing strength.

By relatively large bonding sites, for example in the form of lines, a relatively large bonding area may be provided with a relatively small number of bonding sites, as compared to a bonding pattern of small bonding sites, for example in the form of points, which have to arranged more densely in order to provide the same bonding area as for a pattern of larger bonding size. Thus both bonding area and bonding density are important.

Preferred Example of a Laminate Material

One embodiment of a laminate according to the invention is a nonwoven laminate of at least three fibrous material layers 14, 15 and 16. One outer layer 14 intended to form the outside of the belt is a fibrous material adapted to serve as an attachment surface for the fastening means on the tabs 8 and 11. Examples of nonwoven materials are spunbond, meltblown, carded bonded materials etc. The middle layer 15 should be of a relatively tear strong fibrous material, such as a spunbond or meltblown material comprising continuous filaments. The other outer layer 16, intended to form an inner layer of the belt facing the wearer, should be of a soft and skin friendly fibrous material. Examples of suitable materials are spunbond and meltblown materials, carded bonded materials etc. Examples of polymer materials used in the different fibrous materials may be any suited for this purpose, for example, polypropylene, polyethylene, polyester and/or bicomponent fibers.

The basis weight of the nonwoven laminate can vary between 40 and 150 gsm, preferably between 60 and 120 gsm, and more preferably between 75 and 105 gsm.

One or more layers of the laminate may be creped. According to one embodiment, the outer layer 14 intended to act as the receiving material for the fastening means, especially as a loop material for a hook-and-loop type fastener, is creped. By the creping the loop function of the material is improved.

One nonlimiting example of a laminate according to the invention is a three-layered laminate:

Carded thermobonded material, basis weight 30 gsm, PP fibers of 2.2 dtex;

Spunbond layer, basis weight 40 gsm, PP fibers of 2.2 dtex;

Carded thermobonded material, basis weight 22 gsm, PP fibers of 2.2 dtex.

The spunbond layer is used as the middle layer, the carded material having the highest basis weight is used as the outside of belt, and is adapted to act as loop material for a hook-and-loop type fastener, and the carded material having the lowest basis weight is used as the inner skin-facing side of the belt.

The laminate is bonded by ultrasonic bonding with a bonding area of about 3% and a bonding tightness of about 7 bonding sites per cm$^2$. The tear strength is between 50 and 60 N.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent article comprising:
    a liquid permeable topsheet, a liquid impermeable backsheet, and an absorbent body enclosed therebetween, said article having a front portion, a rear portion and a crotch portion therebetween, and further is provided with
    a pair of belt members attached to one of the rear portion and the front portion of the article and which are intended to be fastened together around a waist of a wearer by fasteners and where the other one of said front portion and said rear portion is provide with fasteners adapted to be fastened to the belt members, in such a way that the article will assume a pant shape, the belt members form a part of a waist portion of the pant,
    the belt members comprise a flexible laminate of at least three layers of fibrous material bonded together in a bonding pattern, one of said layers having an external surface acting as an attachment surface for said fasteners, said bonding pattern having a bonding area of no more than 10%, and a density of bonding sites of between 1 and 15 bonding sites per cm$^2$, and said laminate having a tear strength of at least 22 N;
    wherein said laminate comprises an inner layer of a soft and skin friendly fibrous material, an outer layer that is creped, and a middle layer that is more tear resistant than the inner and outer layers.

2. The absorbent article as claimed in claim 1, wherein said laminate has a tear strength of at least 24N.

3. The absorbent article as claimed in claim 1, wherein said laminate has a tear strength of at least 25N.

4. The absorbent article as claimed in claim 1, wherein said laminate has a tear strength of at least 30N.

5. The absorbent article as claimed in claim 1, wherein said bonding pattern has a bonding area of no more than 5%.

6. The absorbent article as claimed in claim 1, wherein said middle layer comprises continuous filaments.

7. The absorbent article as claimed in claim 1, wherein said middle layer comprises spunbond material.

8. The absorbent article as claimed in claim 1, wherein said middle layer comprises meltblown material.

9. The absorbent article as claimed in claim 1, wherein said outer layer acts as an attachment surface for said fasteners.

10. The absorbent article as claimed in claim 1, wherein said outer layer is a loop material for a hook-and-loop type fastener.

11. The absorbent article as claimed in claim 1, wherein the absorbent article is a diaper.

12. The absorbent article as claimed in claim 1, wherein the absorbent article is an incontinence guard.

13. The absorbent article as claimed in claim 1, wherein the bonding pattern is provided by ultrasonic, laser or heat.

* * * * *